(12) United States Patent
Sokoloff

(10) Patent No.: US 8,152,401 B2
(45) Date of Patent: Apr. 10, 2012

(54) SURGICAL SKIN MARKER WITH DISPOSABLE STERILIZED TIP

(76) Inventor: Daniel Sokoloff, Jupiter, FL (US)

( * ) Notice: Subject to any disclaimer, the term of this patent is extended or adjusted under 35 U.S.C. 154(b) by 988 days.

(21) Appl. No.: 12/154,841

(22) Filed: May 27, 2008

(65) Prior Publication Data

US 2009/0297251 A1  Dec. 3, 2009

(51) Int. Cl.
B43K 5/00 (2006.01)
(52) U.S. Cl. ......................................... 401/198
(58) Field of Classification Search .................. 401/198, 401/199, 202, 132–135, 196; 606/116
See application file for complete search history.

(56) References Cited

U.S. PATENT DOCUMENTS

| | | | |
|---|---|---|---|
| 2,942,577 A | 6/1960 | Solow | |
| 3,481,677 A | 12/1969 | Abrahamson | |
| 3,614,245 A | 10/1971 | Schwartzman | |
| 3,708,235 A | 1/1973 | Kolomeir | |
| 3,781,122 A | 12/1973 | Cheeseman | |
| 3,905,709 A | 9/1975 | Bok | |
| 3,990,451 A | 11/1976 | Gibbs | |
| 4,146,133 A | 3/1979 | Bogorad et al. | |
| D258,911 S | 4/1981 | Sandel | |
| 4,269,526 A * | 5/1981 | Dupre | 401/198 |
| 4,538,612 A * | 9/1985 | Patrick, Jr. | 606/131 |
| 4,610,806 A | 9/1986 | Rosen | |
| 4,665,912 A | 5/1987 | Burton | |
| 4,889,228 A * | 12/1989 | Gueret | 206/209 |
| 5,147,307 A | 9/1992 | Gluck | |
| 5,458,593 A | 10/1995 | Macabasco et al. | |
| 5,496,304 A | 3/1996 | Chasan | |
| 5,665,092 A | 9/1997 | Mangiardi et al. | |
| 5,713,890 A | 2/1998 | Chasan | |
| 5,743,899 A | 4/1998 | Zinreich | |
| 5,776,158 A | 7/1998 | Chou | |
| 5,909,978 A | 6/1999 | Giordano et al. | |
| 5,957,601 A | 9/1999 | Weiss | |
| 5,988,174 A | 11/1999 | Chasan | |
| 6,056,737 A | 5/2000 | Rosen | |
| 6,161,976 A | 12/2000 | Liu | |
| 6,197,034 B1 | 3/2001 | Gvozdic et al. | |
| 6,283,933 B1 | 9/2001 | D'Alessio et al. | |
| 6,436,105 B1 | 8/2002 | Passmore | |
| 6,505,985 B1 | 1/2003 | Hide et al. | |
| 6,551,265 B1 | 4/2003 | Miguel | |

(Continued)

FOREIGN PATENT DOCUMENTS

CN  1486676 A  4/2004

(Continued)

OTHER PUBLICATIONS

Delasco, 2008 Dermatologic Buying Guide, Catalog, p. 169 has surgical skin markers.

(Continued)

*Primary Examiner* — Huyen Le
(74) *Attorney, Agent, or Firm* — Novak Druce + Quigg LLP

(57) ABSTRACT

A surgical skin marker has a handle body and a removably attached marking tip that is provided in a protective sterilized bag. After a single use, the marking tip can be removed and discarded. A new marking tip can be attached for a subsequent surgical procedure or treatment. Such a marker can help maintain a sterile surgical environment while minimizing waste and costs.

17 Claims, 4 Drawing Sheets

U.S. PATENT DOCUMENTS

| | | |
|---|---|---|
| 6,805,669 B2 | 10/2004 | Swanbom |
| 6,860,666 B2 | 3/2005 | Chien |
| 6,893,178 B2 | 5/2005 | Liu |
| 6,923,816 B1 | 8/2005 | Passmore |
| 6,972,022 B1 | 12/2005 | Griffin |
| D538,851 S | 3/2007 | Sandel et al. |
| D552,735 S | 10/2007 | Archambault |
| 2001/0036383 A1 | 11/2001 | Cirlin et al. |
| 2004/0116907 A1 | 6/2004 | Tartaglia |
| 2006/0079910 A1 | 4/2006 | Tartaglia |
| 2006/0228155 A1 | 10/2006 | Butler |
| 2006/0235434 A1 | 10/2006 | Pavich et al. |
| 2007/0020350 A1 | 1/2007 | Numano et al. |
| 2007/0189833 A1 | 8/2007 | San Miguel |
| 2007/0203504 A1 | 8/2007 | Denny et al. |

FOREIGN PATENT DOCUMENTS

| | | |
|---|---|---|
| JP | 58-154772 | 9/1983 |
| WO | WO 2008/013676 A1 | 1/2008 |

OTHER PUBLICATIONS

Delasco Online, TLS Surgical Skin Marker, website: www.delasco.com/pcat/1/Surgery/TLS_Surgical_marker/dlmit039 <visited Mar. 16, 2006>.

Delasco Online, Squeez-Mark Pens, website: www.delasco.com/pcat/1/Surgery/Squeeze_Mark_Pens/dlmis082 <visited Mar. 16, 2006>.

Delasco Online, Surgery website: www.delasco.com/pcat/1/Surgery <visited Mar. 16, 2006>.

* cited by examiner

SURGICAL SKIN MARKER WITH DISPOSABLE STERILIZED TIP

FIELD OF THE INVENTION

The invention relates in general to surgical preparatory instruments and, more particularly, to devices for marking the skin of a patient.

BACKGROUND OF THE INVENTION

Skin markers are commonly used by surgeons in pre-operation preparations. These markers typically have a felt-tip. Using such a marker, a surgeon will mark lines or diagrams on a patient's body indicating where surgical action or other treatment will take place. For example, such markings can be used to guide a surgeon in making an incision in the proper location and/or of the desired size and/or shape. In addition, such markings can guide a surgeon in the placement of sutures, staples or glue for closing an incision.

Because of the potential for contamination with each use and the fear of subsequent transmission if reused, these markers are used only once and are subsequently thrown away. A new marker is used for each pre-operation procedure. However, the constant discarding of an entire marker is wasteful, considering that a substantial portion of the marker should not come into contact with the patient. The repeated replacement of an entire marker can lead to an appreciable increase in expense as well as an unnecessary increase in waste.

Thus, there is a need for a skin marker that can minimize such concerns.

SUMMARY OF THE INVENTION

A first aspect of the invention is directed to a surgical skin marker system that includes a handle body, a sterile tip and an opened container. The handle body has a proximal end region and a distal end region. The distal end region includes a distal end.

The sterile tip includes a working end having a marking agent and an attachment end shaped to attach to the distal end of the handle body. The working end can be made of an absorbent material. In one embodiment, the entire sterile tip can be made of an absorbent material. The tip can have an associated density. The density of the tip can vary across the tip. In one embodiment, the density of the tip near the attachment end can be greater than the density of the tip near the working end.

The opened container encloses at least the working end of the sterile tip and presents the attachment end for attachment to the handle body. As a result, the sterile tip can be attached to the handle body without handling the sterile tip directly with the user's hand, thereby avoiding contamination of the sterile tip during attachment. In one embodiment, the container can be bag having a sterile interior.

A second aspect of the invention is directed to a sterilized tip system. The system includes a bag having a sterile interior and a sterile tip enclosed in the bag. The interior of the bag can be substantially air-tight. In one embodiment, the bag can be sized to receive a single tip. The tip includes a working end having a marking agent and an attachment end.

The bag can include a structurally weakened region so as to facilitate the opening of the bag. In one embodiment, the structurally weakened region can include a pre-tear. In another embodiment, the structurally weakened region can include perforation extending at least partially across the bag. The tip can be oriented in the bag so that the attachment end is located closer to the structurally weakened region than the working end.

In a third respect, aspects of the invention are directed to a method of using a surgical marker. The method includes the step of providing a handle body with a proximal end region and a distal end region, which includes a distal end. A bag is provided that contains a single sterile tip that has a working end having a marking agent and an attachment end shaped to attach to the distal end of the handle body. A portion of the bag is removed so that the attachment end is accessible. The attachment end of tip and the distal end are brought together without directly touching the sterile tip such that the tip is removably attached to the distal end of the handle body so as to form a surgical marker. The bag is removed from the tip. Lastly, the body of a patient is marked using the surgical marker.

DETAILED DESCRIPTION OF EMBODIMENTS OF THE INVENTION

Aspects of the present invention relate to improved surgical markers and associated methods that can facilitate a sterile environment. Embodiments according to aspects of the invention are shown in FIGS. 1-7, but the present invention is not limited to the illustrated structure or application. Further, the following detailed description is intended only as exemplary.

Figure 1:
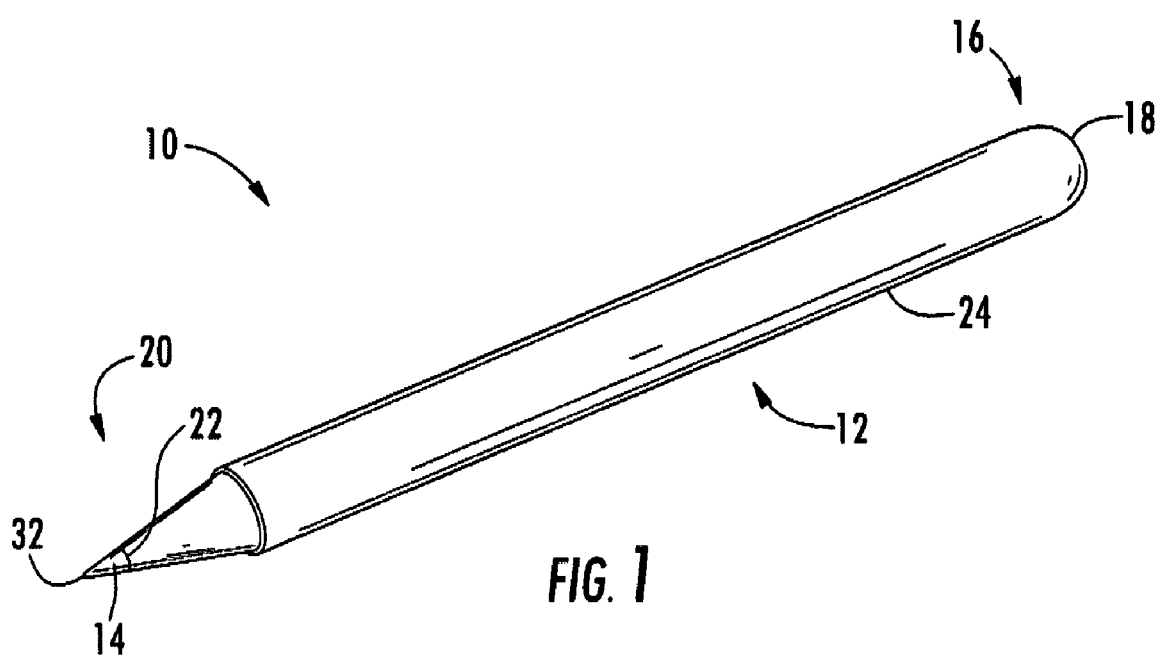
FIG. 1 is a perspective view of a surgical marker in accordance with aspects of the invention.
Figure 2:
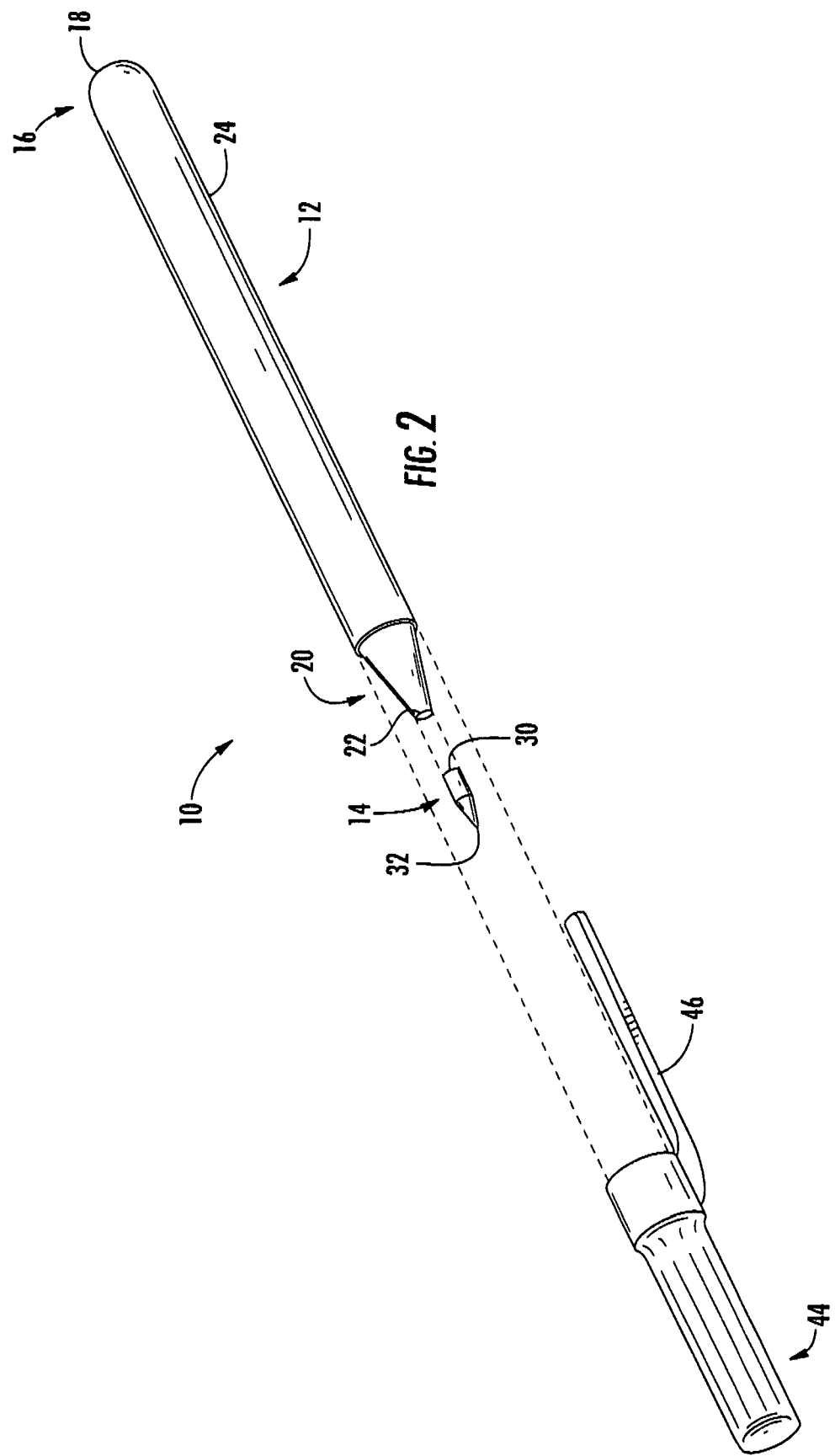
FIG. 2 is an exploded perspective view of a surgical marker in accordance with aspects of the invention.

Referring to FIGS. 1-2, a surgical marker 10 in accordance with aspects of the invention can have a handle body 12 and a marking tip 14 removably attached to the handle body 12. The handle body 12 can have a proximal end region 16, including a proximal end 18, and a distal end region 20, including a distal end 22. The distal end region 20 can be adapted for removable engagement with the tip 14. The handle body 12 can have an outer peripheral surface 24.

The marker 10 can have one or more ergonomic features. For instance, the handle body 12 and/or the outer peripheral surface 24 can be contoured for ergonomic engagement by a user. Alternatively or in addition, additional materials, such as foam or rubber, can be provided on the handle body 12 and/or the outer peripheral surface 10 for ergonomic benefit of the user.

The handle body 12 can have any suitable cross-sectional shape. For instance, the handle body 12 can be generally circular, elliptical, triangular, rectangular or polygonal in cross-section, just to name a few possibilities. The handle body 12 can be substantially straight. Alternatively, the handle body 12 can include one or more bends, curves, angles or other non-straight features. The handle body 12 can be solid, or at least a portion of the handle body 12 can be hollow. The handle body 12 can have any suitable length. The cross-sectional size and/or shape of the handle body 12 may or may not be constant along its length.

The handle body 12 can be made out of any suitable material. The material can be relatively rigid, or at least portions of the handle body 12 can be made of a flexible material. In one embodiment, the handle body 12 can be made of metal, such as stainless steel. In another embodiment, the handle body 12 can be made of plastic. The handle body 12 can be constructed of a material to enable it to be sterilized, such as in an autoclave.

Figure 3:
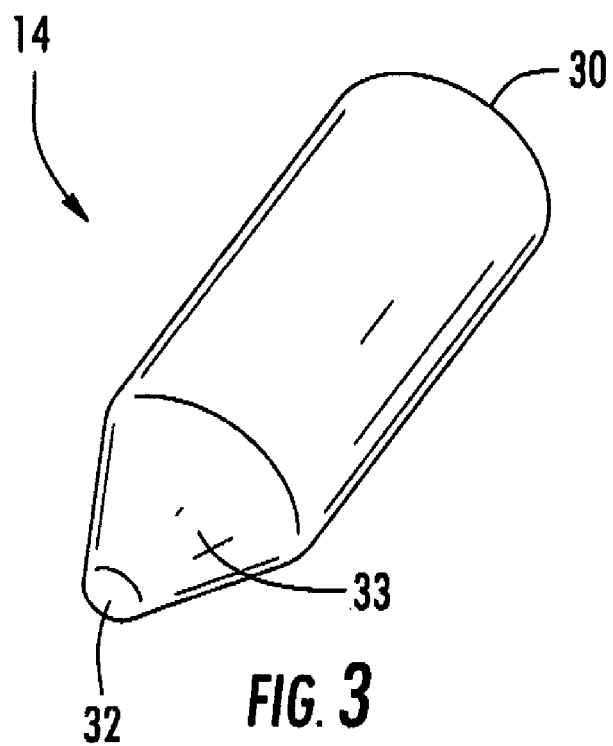
FIG. 3 is a perspective view of a tip in accordance with aspects of the invention, wherein the tip is made entirely of an absorbent material with no other structure.

As noted above, the tip 14 can be removably attached to the handle body 12. In one embodiment, the tip 14 can be made entirely of an absorbent material, such as felt or other suitable material, with no other structure. An example of such a tip is shown in FIG. 3. Alternatively, the tip 14 can, in some instances, include additional structure, such as a different, more rigid material and/or a non-absorbent material or a reinforcing sleeve, to facilitate attachment. The absorbent material can be any suitable material that can absorb or otherwise retain a marking agent for dispensing.

The tip 14 can be sterilized. The tip 14 can have an attachment end 30 and a working end 32. At least the working end 32 of the tip 14 can be pre-wetted, such as at a factory, with a marking agent, such as ink 33. Alternatively, the entire tip 14 can be pre-wetted including the attachment end 30. The marking agent can be any suitable substance to mark a patient's skin. For example, the marking agent can be Gentian Violet ink. Naturally, it is preferred if the marking agent is non-toxic and relatively easy to remove, such as by cleaning the marked area with soap and water. The marking agent used to pre-wet the tip 14 can be the sole source of a marking agent for the assembled surgical marker 10.

There are various manners in which the tip 14 can be removably attached to the handle body 12. Preferably, the tip 14 can be attached to the handle body 12 in such a way that the user does not have to touch the tip 14. It should be noted that the term "removably attached" and variants thereof is intended to mean that attachment and detachment can be achieved relatively quickly by hand and without the assistance of tools.

Figure 4:
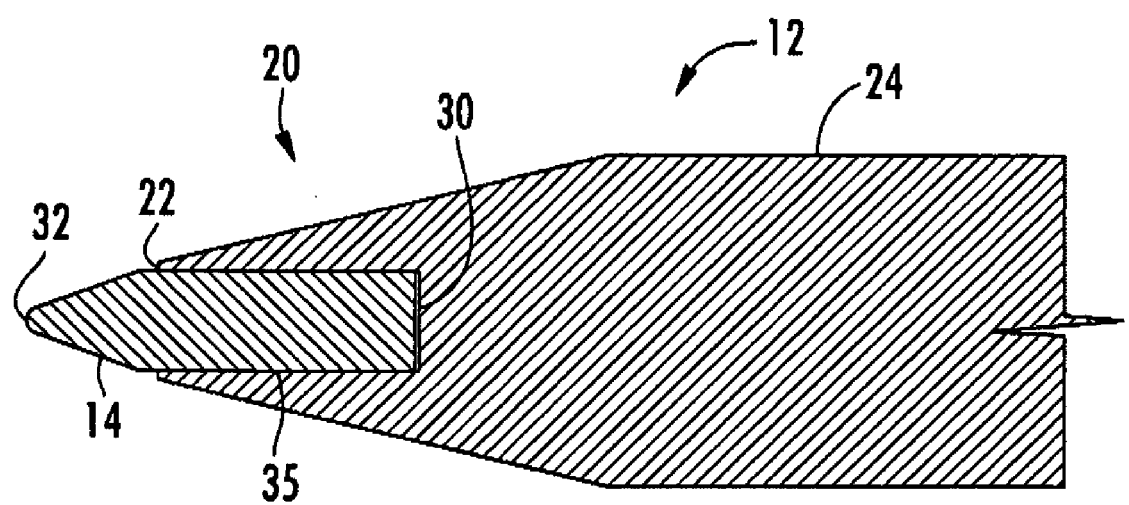
FIG. 4 is a side elevation cross-sectional view of a surgical marker in accordance with aspects of the invention, showing a tip made entirely of an absorbent material and a handle body being removably attached by friction fit.

The tip 14 can be removably attached to the handle body 12 by mechanical engagement. In one embodiment, the tip 14 can be plugged into a receiving recess 35 in the handle body 12, as is generally shown in FIG. 4. The tip 14 and the handle body 12 can be sized so that the tip 14 can be held on the handle body 12 by friction fit, as is also shown in FIG. 4.

The tip 14 can have an associated density. To facilitate insertion and attachment, the density of the tip 14 can vary from the working end 32 to the attachment end 30. More particularly, the density of the tip 14 can be greater near the attachment end 30 compared to the rest of the tip 14.

The surgical marker 10 can also include a protective cap 44 (FIG. 2) to protect the distal end 22 of the handle body 12 when the tip 14 is not attached. The cap 44 can provide a pocket clip 46. The cap 44 can be connected to the handle body 12 so as to enclose a portion of the distal end region 20, including the distal end 22. Use of the cap 44 can minimize the infiltration of dirt, dust, bacteria and other contaminants.

The cap 44 can be retained on the handle body 12 in any suitable manner, such as by a friction fit or a snap fit.

Figure 5:
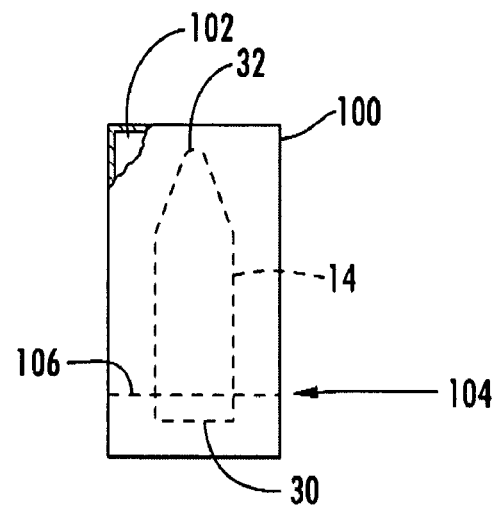
FIG. 5 is a top plan view of a tip enclosed within a bag in accordance with aspects of the invention, showing the bag being perforated to facilitate opening.
Figure 6:
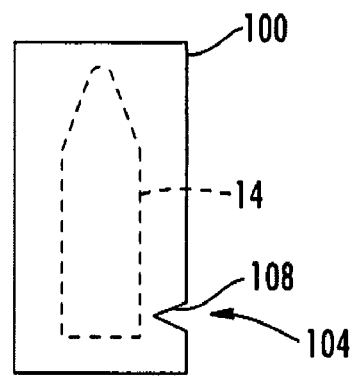
FIG. 6 is a top plan view of a tip enclosed within a bag in accordance with aspects of the invention, showing the bag having a pre-tear to facilitate opening.

In accordance with aspects of the invention, a tip 14 is intended to be used for a single use. Sterile replacement tips 14 can be supplied in various ways. Preferably, the sterile tips 14 can be provided or stored in a sterile container. In one embodiment, individual tips 14 can be provided in a bag 100, as shown in FIGS. 5 and 6. The bag 100 can be made of any suitable material, including, for example, plastic. The bag 100 can be sized to accommodate a single tip 14. The bag 100 can be sized to be small enough to be held between a finger and thumb. The bag 100 can have any suitable shape. The bag 100 can have a sterile interior 102.

The bag 100 can hold a tip 14 air-tightly therein. The bag 100 can preserve sterility of the tip 14. The bag 100 can maintain the moisture of the tip 14 or at least can minimize the loss of moisture. A plurality of bags 100, each containing a single tip 14, can be provided in a box or other storage container (not shown).

The bags 100 can be adapted to facilitate opening. To that end, at least a portion of the bag 100 can include a structurally weakened region 104. In one embodiment, the weakened region 104 can be a pre-tear 108 or notch on a side of the bag, as shown in FIG. 6. Alternatively or in addition, the weakened region 104 can be a perforation 106 extending across at least a portion of the bag 100, as shown in FIG. 5. The tip 14 can be oriented in the bag 100 such that the structurally weakened region 104 is closer to the attachment end 30 of the tip 14, as shown in FIG. 5.

One manner of removably attaching a new tip 14 to the handle body 12 will now be described. A user can hold one of the plastic bags 100 containing a tip 14, such as by grasping it between a finger and thumb. The user can remove a portion of the bag 100, such as by tearing the bag using the structurally weakened region 104 if one is provided, to expose the attachment end 30 of the tip 14.

Figure 7:
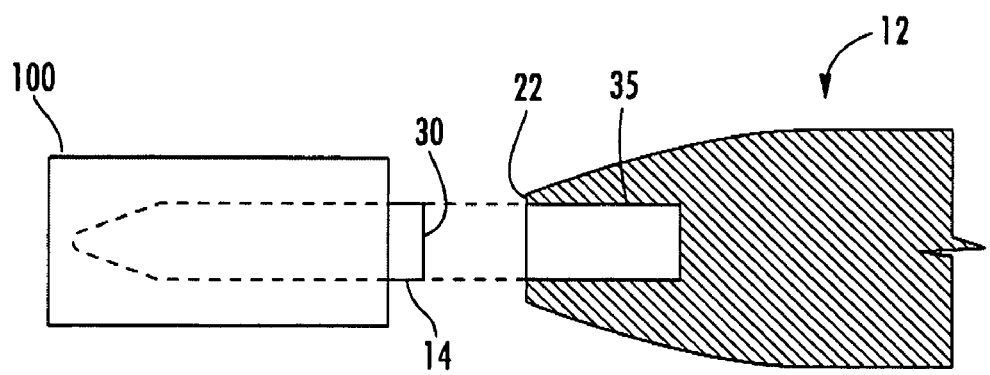
FIG. 7 is a side elevation exploded view of a tip and handle body system in accordance with aspects of the invention, showing the tip being removably attached to the handle body while at least a portion of the tip is in the bag.

Holding a portion of the tip 14 that is still inside the bag 100, the user can bring the handle body 12 and the attachment end 30 of the tip 14 together, as is generally shown in FIG. 7. This bringing together can be achieved without the user ever touching the tip 14 itself, as the user is touching the bag 100 and not the tip 14. The attachment end 30 of the marker 14 can be received in the recess 35 the distal end 22 of the handle body 12. The tip 14 can be retained in the handle body 12 by frictional engagement, such that the tip 14 is removably attached to the handle body 12. Once the tip 14 is attached, the bag 100 can be pulled away from the tip 14. The bag 100 can be discarded, or it can be retained for subsequent use.

With the tip 14 removably attached to the handle body 12, the marker 10 is formed. The user can use the marker 10 as it normally would be used. After use, the user can readily separate the tip 14 from the handle body 12 by hand. The used tip 14 can be discarded. The handle body 12 can be sanitized in any conventional manner.

One manner of using a surgical marker 10 according to aspects of the invention will now be described. Starting with a fully assembled marker 10, the marker 10 can be used like a conventional surgical marker to draw lines and diagrams on the body of a patient, which can be a human or an animal. When these pre-operation preparations are finished, the tip 14 of the marker 10 can be removed and discarded. In one embodiment, the tip 14 of the marker 10 can be removed by hand. For instance, when the tip 14 and the handle body 12 are connected by friction fit, as shown in FIG. 4, the user can hold the handle body 12 with one hand and the tip 14 with the other hand. The user can pull the tip 14 away from the handle body 12. Simultaneously, the user can pull the handle body 12 away from the tip 14, or the user can firmly hold the handle body 12 in place. While the friction fit should be sufficient to hold the tip 14 and the handle body 12 together for regular use of the marker 10, the friction fit should permit the tip 14 and the handle body 12 to be readily separated in the manner described above.

As noted above, the empty, opened bag 100 can be retained for later use. For instance, the user may not want to directly touch the tip 14 during its removal from the handle body 12 because of the potential for transmission of contaminants or to avoid ink marks on the hands. In such case, a portion of the tip 14, including the working end 32, can be received in the empty bag 100. The user can pinch or otherwise grasp the tip 14 through the bag 100. The tip 14 and the handle body 12 can then be separated in any suitable way, such as by pulling the tip 14 and the handle body 12 away from each other.

With the tip 14 removed, the protective cap 44 can be placed on the handle body 12 so as to cover the distal end 22, thereby preventing the infiltration of dirt, dust and other contaminants. The handle body 12 can be cleaned with rubbing alcohol or other disinfectant, or it can be sanitized in an autoclave. When it is time for another operation, the cap 44 can be removed and a new tip 14 attached in any of the manners discussed above. The marker 10 can be used and the above process can be repeated.

It will be appreciated that a surgical marker 10 in accordance with aspects of the invention can provide several advantages. First, the marker configuration can minimize waste, as the handle body 12 can be reused repeatedly while only the relatively small tip 14 is discarded after each use. Second, by reusing a substantial portion of the marker 10, appreciable cost savings can be enjoyed over time. Third, the marker 10 can promote a sterile surgical environment. Indeed, a marker 10 according to aspects of the invention can minimize or even eliminate the need for a doctor to ever touch the tip 14 of the marker 10, which is the only portion that should come into contact with a patient's body. Fourth, the marker 10 eliminates the need to provide a marking agent reservoir associated with the handle body 12, thereby avoiding the associated expense and further minimizing the contamination risk. These and other advantages can be realized with a marker 10 in accordance with aspects of the invention.

It will be understood that the invention is not limited to the specific details described herein, which are given by way of example only, and that various modifications and alterations are possible within the scope of the invention as defined in the following claims.

What is claimed is:

1. A surgical skin marker system comprising:
   a handle body having a proximal end region and a distal end region, the distal end region including a distal end;
   a sterile marker tip including a working end and an attachment end shaped to attach to the distal end of the handle body, said sterile marker tip including at its working end a self-supplied absorbent material pre-wetted with a marking agent that is only provided in the pre-wetted absorbent material; and
   an opened container enclosing at least the working end of the sterile marker tip and presenting the attachment end for attachment to the handle body, whereby the sterile marker tip can be attached to the handle body without handling the sterile marker tip directly with the user's hand, thereby avoiding contamination of the sterile marker tip during attachment, and the pre-wetted sterile marker tip is self-supplied, requiring no marking agent from a reservoir.

2. The marker system of claim 1 wherein the entire sterile marker tip is made of the absorbent material.

3. The marker system of claim 1, wherein the entire sterile marker tip is made substantially of a single, unitary material.

4. The marker system of claim 3 wherein the marker tip has an associated density, wherein the density of the marker tip varies across the marker tip.

5. The marker system of claim 4 wherein the density of the marker tip near the attachment end is greater than the density of the marker tip near the working end.

6. The marker system of claim 1, wherein the container is a bag having a sterile interior.

7. A method of using a surgical marker comprising the steps of:
   providing a handle body with a proximal end region and a distal end region, the distal end region including a distal end;
   providing a bag containing a single sterile marker tip having a working end including a self-supplied absorbent material pre-wetted with a marking agent that is only provided in the pre-wetted absorbent material and an attachment end shaped to attach to the distal end of the handle body;
   removing a portion of the bag so that the attachment end is accessible;
   bringing the attachment end of marker tip and the distal end together without directly touching the sterile marker tip such that the marker tip is removably attached to the distal end of the handle body so as to form a surgical marker;
   removing the bag from the marker tip; and
   marking the body of a patient using the surgical marker.

8. A sterilized marker tip system comprising: a container having a sterile interior; and a sterile marker tip extending from a working end to an attachment end, said sterile marker tip including at its working end a self-supplied absorbent material pre-wetted with a marking agent that is only provided in the pre-wetted absorbent material, the marker tip being enclosed in the container, the container being sized to enclose a single sterile marker tip whereby, upon opening the container, the sterile marker tip can be attached to a marker handle body without handling the sterile marker tip directly with the user's hand, thereby avoiding contamination of the sterile marker tip during attachment, and the self-supplied absorbent material requires no marking agent from a reservoir.

9. The system of claim 8, wherein the attachment end of the marker tip includes a more rigid material to facilitate attachment.

10. The system of claim 8, wherein the attachment end of the marker tip includes a non-absorbent material to facilitate attachment.

11. The system of claim 8, wherein the attachment end of the marker tip includes a sleeve to facilitate attachment.

12. The system of claim 8, wherein the container is formed as a bag that includes a structurally weakened region, whereby opening of the bag is facilitated.

13. The system of claim 12, wherein the structurally weakened region is a pre-tear.

14. The system of claim 12, wherein the structurally weakened region is a perforation extending at least partially across the bag.

15. The system of claim 12, wherein the marker tip is oriented in the bag so that the attachment end is located closer to the structurally weakened region than the working end.

16. The system of claim 12, wherein the bag is sized to receive a single marker tip.

17. The system of claim 8 wherein the interior of the bag is substantially air-tight.

* * * * *